(12) United States Patent
Hargett et al.

(10) Patent No.: US 9,221,195 B2
(45) Date of Patent: *Dec. 29, 2015

(54) METHODS AND APPARATUSES FOR CONSOLIDATING ELASTIC SUBSTRATES

(71) Applicant: The Procter & Gamble Company, Cincinnati, OH (US)

(72) Inventors: Mark Mason Hargett, Liberty Township, OH (US); Jeffrey Alan Darner, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 252 days.

This patent is subject to a terminal disclaimer.

(21) Appl. No.: 13/929,857

(22) Filed: Jun. 28, 2013

(65) Prior Publication Data
US 2014/0001681 A1  Jan. 2, 2014

Related U.S. Application Data

(60) Provisional application No. 61/665,933, filed on Jun. 29, 2012.

(51) Int. Cl.
*A61F 13/15* (2006.01)
*B29B 13/00* (2006.01)
*B32B 38/18* (2006.01)

(52) U.S. Cl.
CPC ........... *B29B 13/00* (2013.01); *A61F 13/15593* (2013.01); *A61F 13/15723* (2013.01);
(Continued)

(58) Field of Classification Search
CPC .............. B65H 2406/362; B65H 2406/3622; B65H 2406/363; B65H 2404/1362; B65H 2404/1374; B65H 2301/51537; Y10T 156/10; Y10T 156/1052; Y10T 156/1084; Y10T 156/12; Y10T 156/17; B32B 38/1858
See application file for complete search history.

(56) References Cited

U.S. PATENT DOCUMENTS 3,848,594 A   11/1974  Buell
3,860,003 A    1/1975  Buell
(Continued)

FOREIGN PATENT DOCUMENTS

EP    0 565 606 B1   3/1995
EP    2 332 505 A1   6/2011
(Continued)

OTHER PUBLICATIONS

PCT/International Search Report, dated Oct. 7, 2013, 7 pages.
(Continued)

*Primary Examiner* — Carson Gross
(74) *Attorney, Agent, or Firm* — Sarah M. DeCristofaro; Abbey A. Lopez

(57) ABSTRACT

The method includes rotating a drum about an axis of rotation. A discrete length of elastic substrate is positioned on the outer circumferential surface of the rotating drum, wherein the discrete length of elastic substrate is in a stretched state and defines a first length. The discrete length of elastic substrate may be defined by a first end region, a second end region, and a central region separating the first and second end regions. The method may comprise applying vacuum pressure to the first, second, and central regions of the discrete length of elastic substrate. Vacuum pressure may be reduced on the first and second end regions such that the discrete length of elastic substrate consolidates to a second length that is less than the first length.

16 Claims, 14 Drawing Sheets

(52) U.S. Cl.
CPC ....... *A61F13/15731* (2013.01); *B32B 38/1858* (2013.01); *B65H 2406/33* (2013.01); *B65H 2801/57* (2013.01)

(56) References Cited

U.S. PATENT DOCUMENTS

| | | |
|---|---|---|
| 3,911,173 A | 10/1975 | Sprague, Jr. |
| 3,929,135 A | 12/1975 | Thompson |
| 4,324,246 A | 4/1982 | Mullane et al. |
| 4,342,314 A | 8/1982 | Radel et al. |
| 4,381,781 A | 5/1983 | Sciaraffa et al. |
| 4,463,045 A | 7/1984 | Ahr et al. |
| 4,573,986 A | 3/1986 | Minetola et al. |
| 4,609,518 A | 9/1986 | Curro et al. |
| 4,610,678 A | 9/1986 | Weisman et al. |
| 4,629,643 A | 12/1986 | Curro et al. |
| 4,662,875 A | 5/1987 | Hirotsu et al. |
| 4,673,402 A | 6/1987 | Weisman et al. |
| 4,695,278 A | 9/1987 | Lawson |
| 4,785,996 A | 11/1988 | Ziecker et al. |
| 4,795,454 A | 1/1989 | Dragoo |
| 4,808,178 A | 2/1989 | Aziz et al. |
| 4,834,735 A | 5/1989 | Alemany et al. |
| 4,842,666 A | 6/1989 | Werenicz |
| 4,846,815 A | 7/1989 | Scripps |
| 1,857,067 A | 8/1989 | Wood et al. |
| 4,888,231 A | 12/1989 | Angstadt |
| 4,894,060 A | 1/1990 | Nestegard |
| 4,909,803 A | 3/1990 | Aziz et al. |
| 4,925,520 A | 5/1990 | Beaudoin et al. |
| 4,946,527 A | 8/1990 | Battrell |
| 4,963,140 A | 10/1990 | Robertson et al. |
| 1,988,344 A | 1/1991 | Reising et al. |
| 4,988,345 A | 1/1991 | Reising |
| 5,006,394 A | 4/1991 | Baird |
| 5,137,537 A | 8/1992 | Herron et al. |
| 5,147,345 A | 9/1992 | Young et al. |
| 5,151,092 A | 9/1992 | Buell et al. |
| 5,221,274 A | 6/1993 | Buell et al. |
| 5,260,345 A | 11/1993 | Desmarais et al. |
| 5,342,338 A | 8/1994 | Roe |
| 5,387,207 A | 2/1995 | Dyer et al. |
| 5,518,801 A | 5/1996 | Chappell et al. |
| 5,562,646 A | 10/1996 | Goldman et al. |
| 5,571,096 A | 11/1996 | Dobrin et al. |
| 5,580,411 A | 12/1996 | Nease et al. |
| 5,595,567 A | 1/1997 | King et al. |
| 5,624,427 A | 4/1997 | Bergman et al. |
| 5,650,222 A | 7/1997 | Desmarais et al. |
| 5,669,894 A | 9/1997 | Goldman et al. |
| 5,674,216 A | 10/1997 | Buell et al. |
| 5,691,035 A | 11/1997 | Chappell et al. |
| 5,693,165 A | 12/1997 | Schmitz |
| 5,723,087 A | 3/1998 | Chappell et al. |
| 5,735,840 A | 4/1998 | Kline et al. |
| 5,865,823 A | 2/1999 | Curro |
| 5,916,663 A | 6/1999 | Chappell et al. |
| 5,928,212 A | 7/1999 | Kline et al. |
| 5,941,864 A | 8/1999 | Roe |
| 6,004,306 A | 12/1999 | Roe et al. |
| 6,010,491 A | 1/2000 | Roe et al. |
| 6,027,483 A | 2/2000 | Chappell et al. |
| 6,251,097 B1 | 6/2001 | Kline et al. |
| 6,414,215 B1 | 7/2002 | Roe |
| 6,432,098 B1 | 8/2002 | Kline et al. |
| 6,441,266 B1 | 8/2002 | Dyer et al. |
| 6,573,423 B1 | 6/2003 | Herrlein et al. |
| 6,596,108 B2 | 7/2003 | McCabe |
| 6,677,258 B2 | 1/2004 | Carroll et al. |
| 8,377,249 B2 | 2/2013 | Gill |
| 2004/0162536 A1 | 8/2004 | Becker et al. |
| 2004/0167486 A1 | 8/2004 | Busam et al. |
| 2005/0215972 A1 | 9/2005 | Roe et al. |
| 2005/0215973 A1 | 9/2005 | Roe et al. |
| 2005/0275148 A1 | 12/2005 | Beaudoin et al. |
| 2006/0189956 A1 | 8/2006 | Catalan |
| 2007/0078427 A1 | 4/2007 | Raycheck et al. |
| 2007/0093769 A1 | 4/2007 | Kline et al. |
| 2007/0142798 A1 | 6/2007 | Goodlander et al. |
| 2007/0142806 A1 | 6/2007 | Roe et al. |
| 2007/0219521 A1 | 9/2007 | Hird et al. |
| 2007/0287348 A1 | 12/2007 | Autran et al. |
| 2007/0287982 A1 | 12/2007 | Lodge et al. |
| 2007/0287983 A1 | 12/2007 | Lodge et al. |
| 2009/0294044 A1 | 12/2009 | Gill |
| 2010/0252603 A1 | 10/2010 | Gill |
| 2011/0139657 A1 | 6/2011 | Hird et al. |
| 2011/0139658 A1 | 6/2011 | Hird et al. |
| 2011/0139659 A1 | 6/2011 | Hird et al. |
| 2011/0139662 A1 | 6/2011 | Hird et al. |
| 2011/0152812 A1 | 6/2011 | Hird et al. |

FOREIGN PATENT DOCUMENTS

| | | |
|---|---|---|
| WO | WO 95/16746 | 6/1995 |
| WO | WO 00/02727 A1 | 1/2000 |
| WO | WO 2006/015141 | 2/2006 |
| WO | WO 2009/027892 A1 | 3/2009 |
| WO | WO 2009/146307 A1 | 12/2009 |

OTHER PUBLICATIONS

U.S. Appl. No. 13/929,854, filed Jun. 28, 2013, Mark Mason Hargett.

METHODS AND APPARATUSES FOR CONSOLIDATING ELASTIC SUBSTRATES

This application claims priority to U.S. Provisional Application Ser. No. 61/665,933, filed Jun. 29, 2012, which is hereby incorporated by reference in its entirety.

FIELD OF THE INVENTION

The present disclosure relates generally to vacuum drums, and, more particularly, relates to methods and apparatuses using vacuum drums to consolidate regions of an elastic substrate.

BACKGROUND OF THE INVENTION

Along an assembly line, various types of articles, such as for example, diapers and other absorbent articles, may be assembled by adding components to and/or otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. In some cases, individual components created from advancing web or webs are combined with other individual components created from other advancing web or webs. Webs of material and component parts used to manufacture diapers may include: backsheets, topsheets, leg cuffs, waistbands, absorbent core components, front and/or back ears, fastening components, and various types of elastic webs and components such as leg elastics, barrier leg cuff elastics, stretch side panels, and waist elastics. Once the desired component parts are assembled, the advancing web(s) and component parts are subjected to a final knife cut to separate the web(s) into discrete diapers or other absorbent articles.

Some production operations are configured to advance and cut continuous lengths of elastic substrate into discrete lengths of elastic substrate. The discrete lengths of elastic substrate may be used, for example, as barrier leg cuff elastics, elastic waistbands, or front and/or back ears for absorbent articles. In some operations, an elastic substrate may advance on a vacuum drum in a stretched state. The elastic substrate may be cut into discrete lengths of elastic substrate while advancing on the drum. The drum may be configured with vacuum to hold the discrete lengths of elastic substrate in a stretched state on the outer circumferential surface of the drum. The discrete lengths of elastic substrate may have a first end region and a second end region separated by a central region. In some processes, the discrete length of elastic substrate may be uniformly stretched from the first end region to the second end region.

In some instances, the real and/or perceived fit of the absorbent article on the wearer may be improved by providing different regions of the discrete length of elastic substrate with different amounts of stretch. For example, in the case of an elastic waistband, it may be useful for the center of the elastic waistband to have more stretch than the ends of the elastic waistband in order to hold the absorbent article on the wearer while not being too tight as to cause discomfort around the hips of the wearer. Accordingly, it may be desirable to provide a process and apparatus for consolidating regions of a stretched discrete length of elastic substrate while maintaining stretch in at least one region of the discrete length of elastic substrate.

In some processes, different amounts of stretched may be imparted to discrete lengths of elastic substrate by hand. However, absorbent articles may be manufactured in high speed production operations. Therefore, there exists a need to impart different amounts of stretch to discrete lengths of elastic substrate in a manufacturing process operating at high speeds. In other processes, different amounts of stretch may be imparted to discrete lengths of elastic substrate by advancing the substrate through a series of operations, which adds cost and complexity to the manufacturing process. Therefore, it may be beneficial to provide a simplified process and apparatus for consolidating regions of a discrete length of elastic substrate in a high speed manufacturing operation.

SUMMARY OF THE INVENTION

In some aspects, the present disclosure relates to a method for forming a discrete length of elastic substrate. The method may comprise the steps of: rotating a drum about a rotation axis, the drum having an outer circumferential surface; positioning a discrete length of elastic substrate on the outer circumferential surface of the rotating drum, wherein the discrete length of elastic substrate is in a stretched state and defines a first length, the discrete length of elastic substrate having a first end region, a second end region, and a central region separating the first and second end regions; applying vacuum pressure to the first end region, second end region, and central region of the discrete length of elastic substrate, wherein the vacuum pressures in the first end region, second end region, and central region of the discrete length of elastic substrate are less than atmospheric air pressure; and increasing the vacuum pressure on the first and second end regions such that the discrete length of elastic substrate consolidates to a second length less than the first length.

In some aspects, the present disclosure relates to an apparatus for making a discrete length of elastic substrate. The apparatus comprises a drum rotatable about an axis of rotation. The drum may have an outer circumferential surface. The apparatus may comprise a plurality of vacuum apertures in the outer circumferential surface of the drum, wherein the vacuum apertures are arranged into a first vacuum region, a second vacuum region, and a central vacuum region separating the first and second vacuum regions. The drum may also comprise a first vacuum compartment located radially inward from the outer circumferential surface of the drum, wherein the vacuum apertures in the first vacuum region are in gaseous communication with the first vacuum compartment. The drum may also comprise a second vacuum compartment located radially inward from the outer circumferential surface of the drum, wherein the vacuum apertures in the second vacuum region are in gaseous communication with the second vacuum compartment, wherein the first and second vacuum compartments each comprise a vacuum release aperture. The drum may also comprise a third vacuum compartment located radially inward from the outer circumferential surface of the drum, wherein the vacuum apertures in the central vacuum region are in gaseous communication with the third vacuum compartment, wherein the first, second, and third vacuum compartments each comprise a vacuum channel, each vacuum channel having a vacuum channel opening. The drum may also comprise a vacuum control member located adjacent the vacuum channel openings and the vacuum release apertures, the vacuum control member comprising a plurality of vacuum control apertures.

DETAILED DESCRIPTION OF THE INVENTION

Figure 1A:
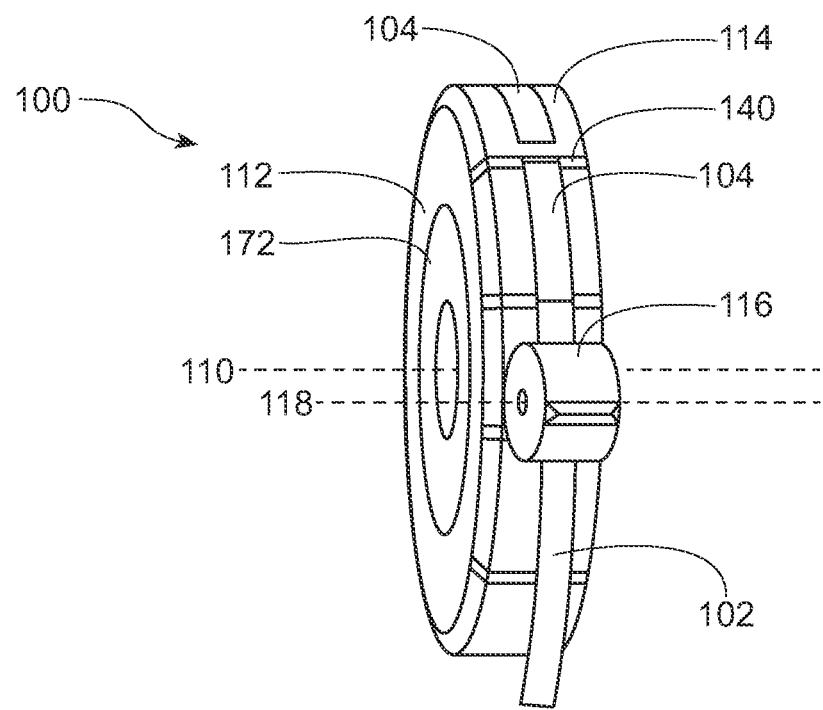
FIG. 1A is a schematic, perspective front view of an apparatus for reducing stretch in regions of an advancing discrete length of elastic substrate.

The following definitions may be useful in understanding the present disclosure:

"Absorbent article" is used herein to refer to consumer products whose primary function is to absorb and retain soils and wastes.

"Diaper" is used herein to refer to an absorbent article generally worn by infants and incontinent persons about the lower torso.

"Disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

"Substrate" is used herein to describe a material which is primarily two-dimensional (i.e. in an XY plane) and whose thickness (in a Z direction) is relatively small (i.e. 1/10 or less) in comparison to the material's length (in an X direction) and width (in a Y direction). Non-limiting examples of substrates include a layer or layers or fibrous materials, films and foils such as plastic films or metallic foils that may be used alone or bonded to one or more web, layer, film and/or foil to form a layered elastic substrate. As such, a web is a substrate.

"Nonwoven" refers herein to a material made from continuous (long) filaments (fibers) and/or discontinuous (short) filaments (fibers) by processes such as spunbonding, melt-blowing, and the like. Nonwovens do not have a woven or knitted filament pattern.

"Machine direction" (MD) is used herein to refer to the direction of flow of an elastic substrate through a process.

"Cross direction" (CD) is used herein to refer to a direction that is not parallel with, and usually perpendicular to, the machine direction in the XY plane of the material.

"Stretchable" refers to materials that are capable of extending in at least one direction to a certain degree without undue rupture.

"Elastic," "elastomer" or "elastomeric" refers to any material that upon application of a force to the material's relaxed, initial length can stretch or elongate to an elongated length more than 10% greater than the material's initial length and will substantially recover back to about the material's initial length upon release of the applied force. The term "inelastic" refers herein to any material that does not fall within the definition of "elastic."

"Radial" means a direction running from an axis of rotation of a drum toward the outer circumferential surface of the drum.

"Vacuum pressure" refers to a pressure applied to a discrete length of elastic substrate from radially inward from an outer circumferential surface of a drum. Vacuum pressure is a pressure below atmospheric air pressure.

"Consolidation" and "consolidated" refers to a material undergoing a reduction in elongation from a first stretched length to a second stretched length that is less than the first stretched length and greater than zero.

"Relaxed state" defines a length of material when not stretched by an applied force.

In the context of the present description, an elongation of 0% refers to a material in relaxed state having a relaxed length of L, and elongation of 150% represents 2.5× the relaxed length, L, of the material. For example, an elastic strand having a relaxed length of 100 millimeters would have a length of 250 millimeters at 150% elongation. An elastic strand having a relaxed length of 100 millimeters would have a length of 180 millimeters at 80% elongation.

"Radial" means a direction running from an axis of rotation of a drum toward the outer circumferential surface of the drum.

The present disclosure relates to methods and apparatuses for forming an elastic substrate for manufacturing absorbent articles, and more particularly, methods and apparatuses for reducing stretch in regions of an advancing discrete waistband. Particular exemplary configurations of the apparatuses and methods disclosed herein provide for consolidating regions of a stretched discrete waistband while maintaining stretch in at least one region of the discrete waistband. It is to be appreciated that the apparatus disclosed herein may be used to consolidate or relax regions of a stretched discrete waistband while maintaining stretch in at least one region. Although the methods and apparatuses herein are discussed below in the context of manufacturing discrete waistbands for diapers, it is to be appreciated that the methods and apparatuses herein can be applied to other elastic components used on diapers as well as other types of absorbent articles.

An exemplary apparatus may include a drum and a cutting member located adjacent the drum. The drum may include an outer circumferential surface and may include vacuum compartments located radially inward from the outer circumferential surface of the drum and vacuum apertures located in the outer circumferential surface of the drum. The vacuum apertures may be arranged into a first vacuum region and a second vacuum region separated by a central vacuum region in the outer circumferential surface of the drum. The vacuum apertures in the first vacuum region may be in gaseous communication with a first vacuum compartment; the vacuum apertures in the second vacuum region may be in gaseous communication with a second vacuum compartment; and the vacuum apertures in the central vacuum region may be in gaseous communication with a central vacuum compartment.

During operation, the drum rotates about an axis of rotation and a continuous length of elastic substrate advances onto the outer circumferential surface of the drum in a stretched state. The cutting member located adjacent the drum may cut the continuous length of elastic substrate into stretched discrete lengths of elastic substrate having a first length. The discrete lengths of elastic substrate may be defined by a first end region and a second end region separated by a central region. The discrete length of elastic substrate may be positioned on the outer circumferential surface of the drum such that the first end region is positioned on a first vacuum region, the central region is positioned on a central vacuum region, and the second end region is positioned on a second vacuum region. Vacuum pressure may be applied to the first, second, and central vacuum compartments in order to hold the discrete length of elastic substrate in a stretched state on the outer circumferential surface of the drum after being cut from the continuous length of elastic substrate. As the discrete length of elastic substrate advances on the drum, vacuum pressure in the first and second vacuum regions may be increased in order to consolidate the discrete length of elastic substrate from the first length to a second length that is shorter than the first length.

The first, second, and central vacuum compartments may be configured to apply different vacuum pressures to different regions of the discrete length of elastic substrate at different times. For example, the apparatus may be configured to apply a first vacuum pressure in the first end region, a second vacuum pressure in the second end region, and a third vacuum pressure in the central region of the discrete length of elastic substrate. In some exemplary configurations, the first vacuum pressure and second vacuum pressure may be increased and the third vacuum pressure may be held constant. And, in some configurations, the first and second vacuum pressures may be increased above the third vacuum pressure. As a result, the discrete length of elastic substrate may consolidate in the first and second end regions while the central region is maintained at a constant elongation. The discrete length of elastic substrate may consolidate from the first length to a second length that is shorter than the first length. In some exemplary configurations, the first and second vacuum pressures may be decreased after the discrete length of elastic substrate consolidates from a first length to a second length in order to hold the discrete length of elastic substrate at the second length on the outer circumferential surface of the drum and to stop the discrete length of elastic substrate from further consolidating.

Although the methods and apparatuses herein may be configured for various types of discrete lengths of elastic substrate, the methods and apparatuses herein are discussed below in the context of manufacturing absorbent articles. In particular, the methods and apparatuses are discussed in the context of making discrete lengths of elastic substrate in the form of elastic waistbands for diapers. While the present disclosure relates mainly making elastic components such as waistbands for diapers, it is to be appreciated that the methods and apparatuses disclosed herein can also be applied to other discrete lengths of elastic substrate used on diapers as well as other types of absorbent articles. Other elastic components used on an absorbent article may include, for example, ears or side panels, leg cuffs, and topsheets.

Figure 1B:
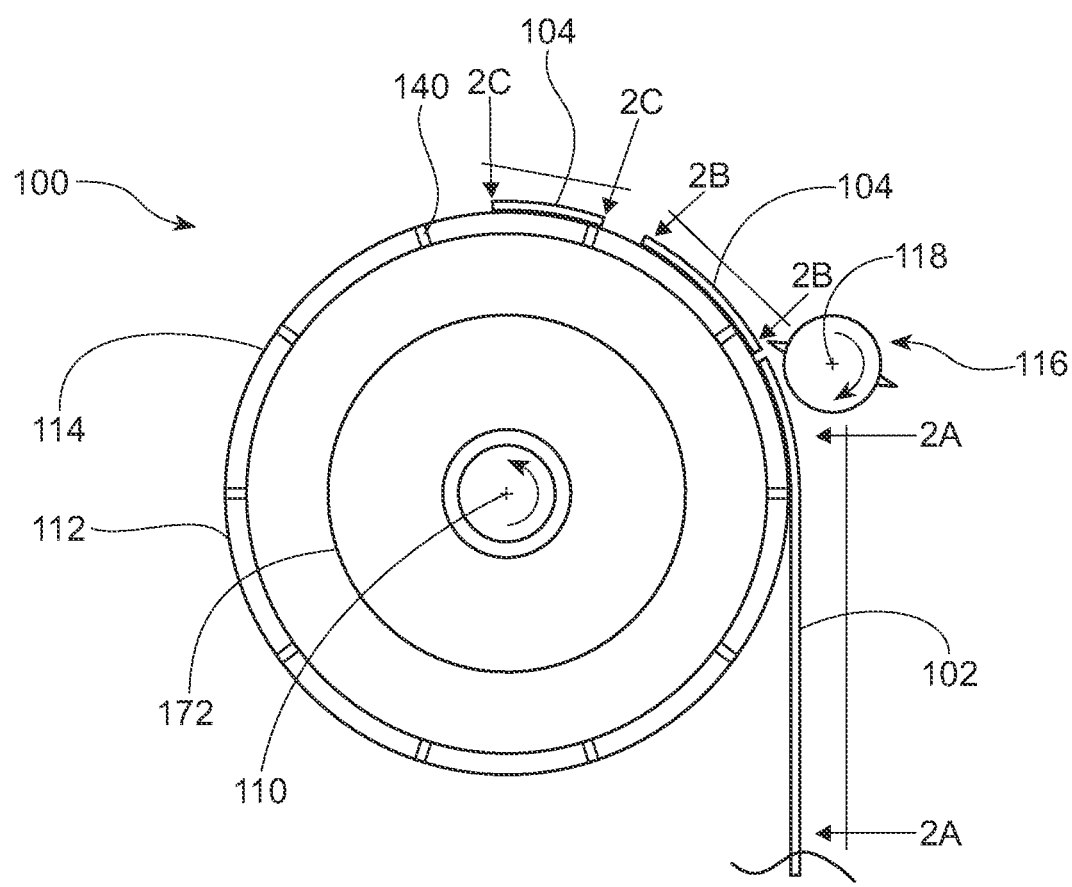
FIG. 1B is a schematic, side elevation view of an apparatus for reducing stretch in regions of an advancing discrete length of elastic substrate.

FIGS. 1A and 1B show an exemplary apparatus 100 used to consolidate regions of an advancing discrete length of elastic substrate 104. As shown in FIGS. 1A and 1B, the apparatus 100 includes a drum 112 rotatable about an axis of rotation 110. The drum 112 may include an outer circumferential surface 114. The apparatus 100 may also include a cutting member 116 rotatable about an axis of rotation 118 and located adjacent the drum 112 for cutting the continuous length of elastic substrate 102 into discrete lengths of elastic substrate 104 while advancing on the outer circumferential surface 114 of the drum 112. As discussed in more detail below, the drum 112 may be configured to consolidate the discrete length of elastic substrate 104 as it advances on the drum 112 after being cut, while maintaining stretch in at least one region of the discrete length of elastic substrate 104. The drum 112 may include anvils 140 located in the outer circumferential surface 114 of the drum 112 for receiving a cut from the cutting member 116.

Figure 2A:
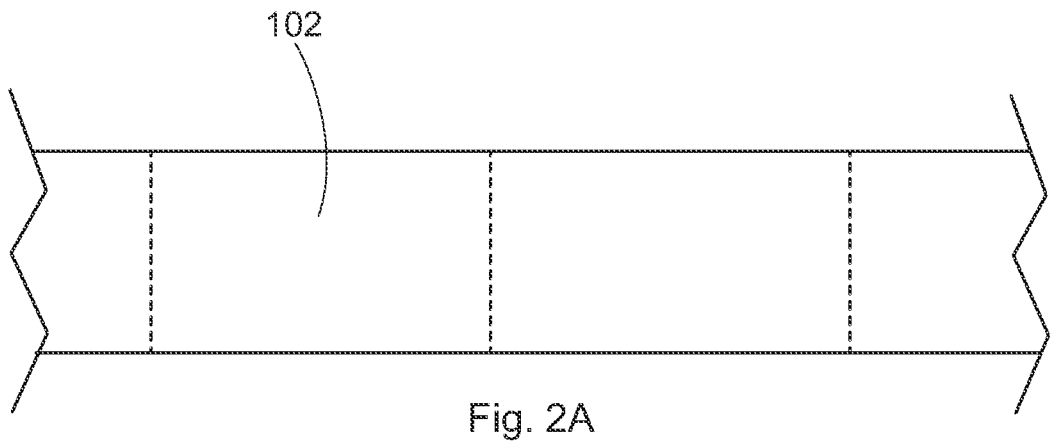
FIG. 2A is a continuous length of elastic substrate from FIG. 1B taken along line 2A-2A.
Figure 2B:
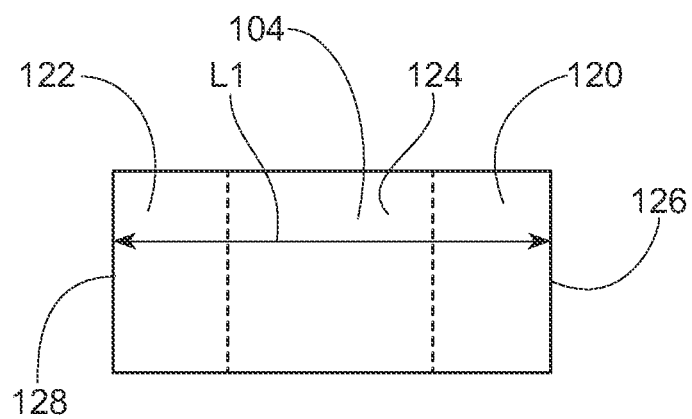
FIG. 2B is a discrete length of elastic substrate from FIG. 1B taken along line 2B-2B.
Figure 2C:
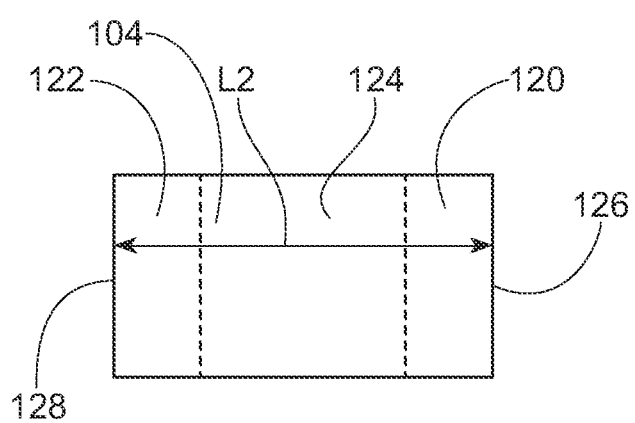
FIG. 2C is a discrete length of elastic substrate with reduced stretch from FIG. 1B taken along line 2C-2C.

FIG. 2A shows an exemplary continuous length of elastic substrate 102 before being cut into discrete lengths of elastic substrate 104. FIG. 2B shows an exemplary discrete length of elastic substrate 104 after being cut from the continuous length of elastic substrate 102. It is to be appreciated that FIG. 2A is a view taken along line 2A-2A from FIG. 1B and FIG. 2B is a view taken along line 2B-2B from FIG. 1B. With reference to FIGS. 1A, 1B, 2A, and 2B, the continuous length of elastic substrate 102 may be cut by the cutting member 116 into discrete length of elastic substrate 104 while advancing on the drum 112. As shown in FIG. 2B, a discrete length of elastic substrate 104 may be defined by a first end region 120, a second end region 122, and a central region 124 separating the first and second end regions 120 and 122, respectively. The discrete length of elastic substrate 104 may also be defined by a length L1 that extends from a first end 126 to a second end 128 of the discrete length of elastic substrate 104. After the discrete length of elastic substrate 104 is cut, the vacuum pressure may be increased in the first and second end regions 120 and 122 in order to consolidate the discrete length of elastic substrate 104 in the first and second end regions 120 and 122. The discrete length of elastic substrate 104 may be consolidated from the first length L1 shown in FIG. 2B to a second length L2 shown in FIG. 2C that is shorter than the first length L1. It is to be appreciated that FIG. 2C is a view taken along line 2C-2C from FIG. 1B.

Figure 3:
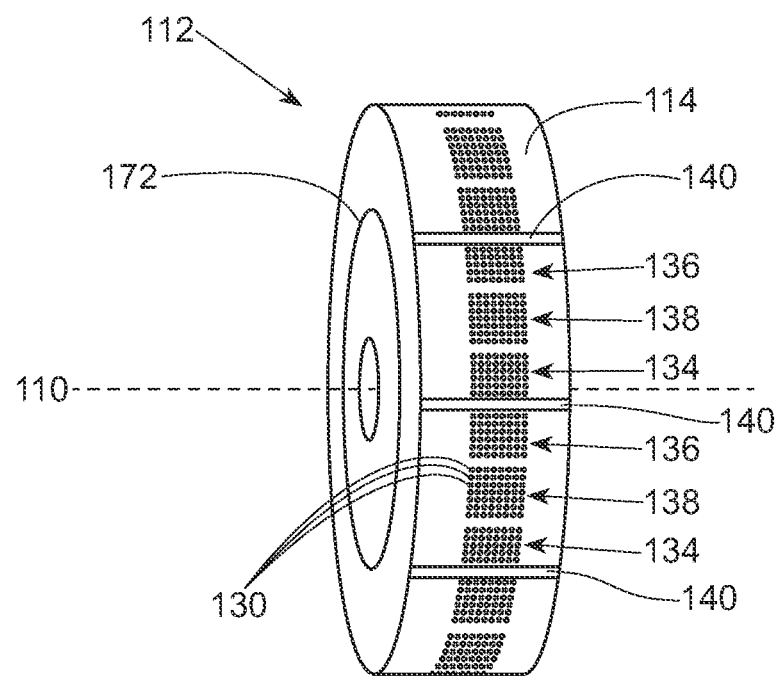
FIG. 3 is a schematic, perspective view of a drum.

As shown in FIG. 3, the drum 112 may include an outer circumferential surface 114 having a plurality of vacuum apertures 130. The vacuum apertures 130 may be arranged into first vacuum regions 134, second vacuum regions 136, and central vacuum regions 138 in the outer circumferential surface 114 of the drum 112. The drum 112 may also comprise anvils 140 located between adjacent first and second vacuum regions 134 and 136. The anvils 140 provide a durable cutting surface for the cutting member 116 as shown in FIG. 1A. The anvils 140 may be made of a durable material such as, for example, tool steel or carbide that can withstand heat and pressure from the cutting member 116. As discussed in more detail below, the drum 112 may also comprise a plurality of vacuum compartments located radially inward from the outer circumferential surface 114 of the drum 112. The vacuum apertures 130 may be in gaseous communication with a vacuum compartment. Each vacuum compartment may be configured to apply a different vacuum pressure to the first, second, and central regions of the discrete length of elastic substrate. It is to be appreciated that in some exemplary configurations, the spacing, size, and shape of the vacuum apertures 130 may be configured in various ways.

Figure 4A:
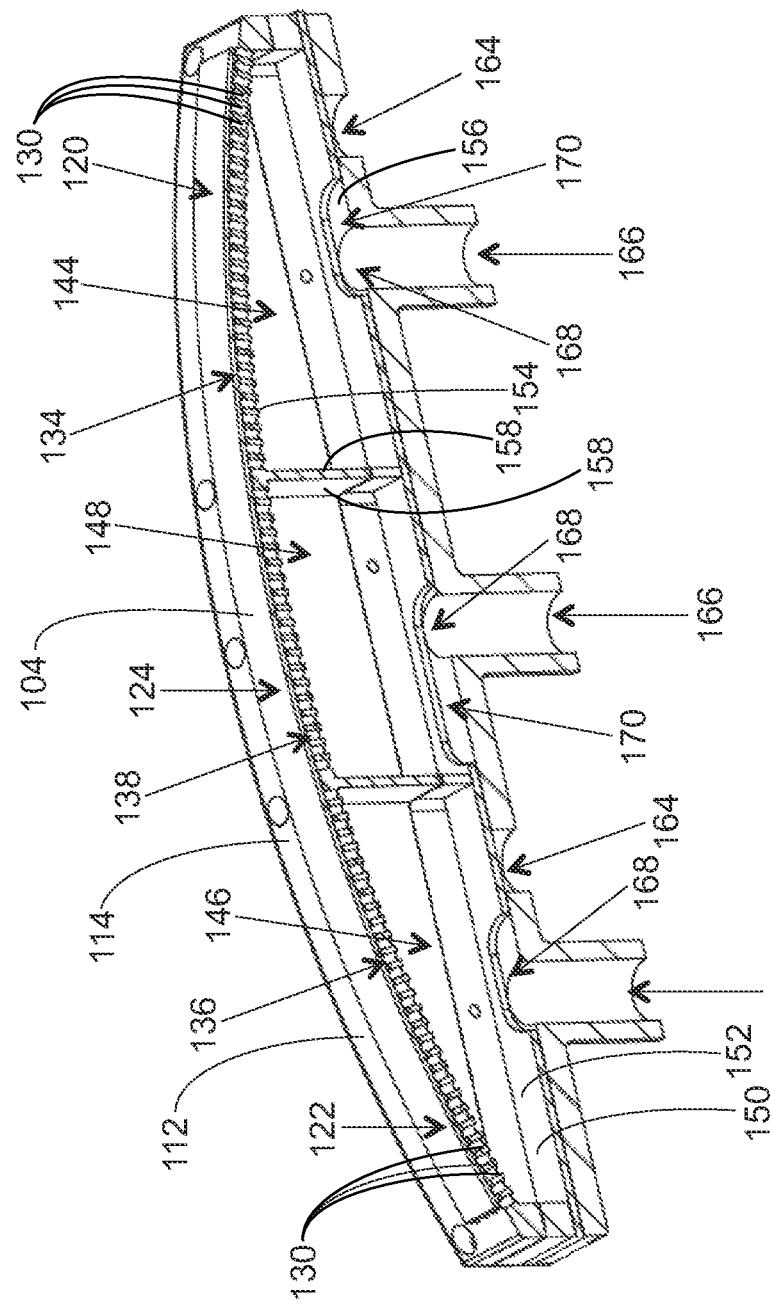
FIGS. 4A is a partial, cross-sectional view of a drum having a slide bar vacuum control member.

As shown in FIG. 4A, a first vacuum region 134 may be in gaseous communication with a first vacuum compartment 144; a second vacuum region 136 may be in gaseous communication with a second vacuum compartment 146; and a central vacuum region 138 may be in gaseous communication with a central vacuum compartment 148. Each of the first, second, and central vacuum compartments 144, 146, and 148 may be defined by a top surface 154, a bottom surface 156, and side walls 158. The first, second, and central vacuum compartments 144, 146, and 148 may be in gaseous communication with vacuum apertures 130 in the top surface 154 and vacuum channel openings 168 in the bottom surface 156. In addition, as shown in FIG. 4A, the first and second vacuum compartments 144 and 146 may be in gaseous communication with a vacuum release aperture 164. It is to be appreciated that vacuum pressure is applied to the first, second, and central vacuum compartments 144, 146, and 148 through vacuum channels 166 at the vacuum channel openings 168 while the vacuum release apertures 164 expose the first and second vacuum compartments 144 and 146 to atmospheric air pressure.

Figure 4B:
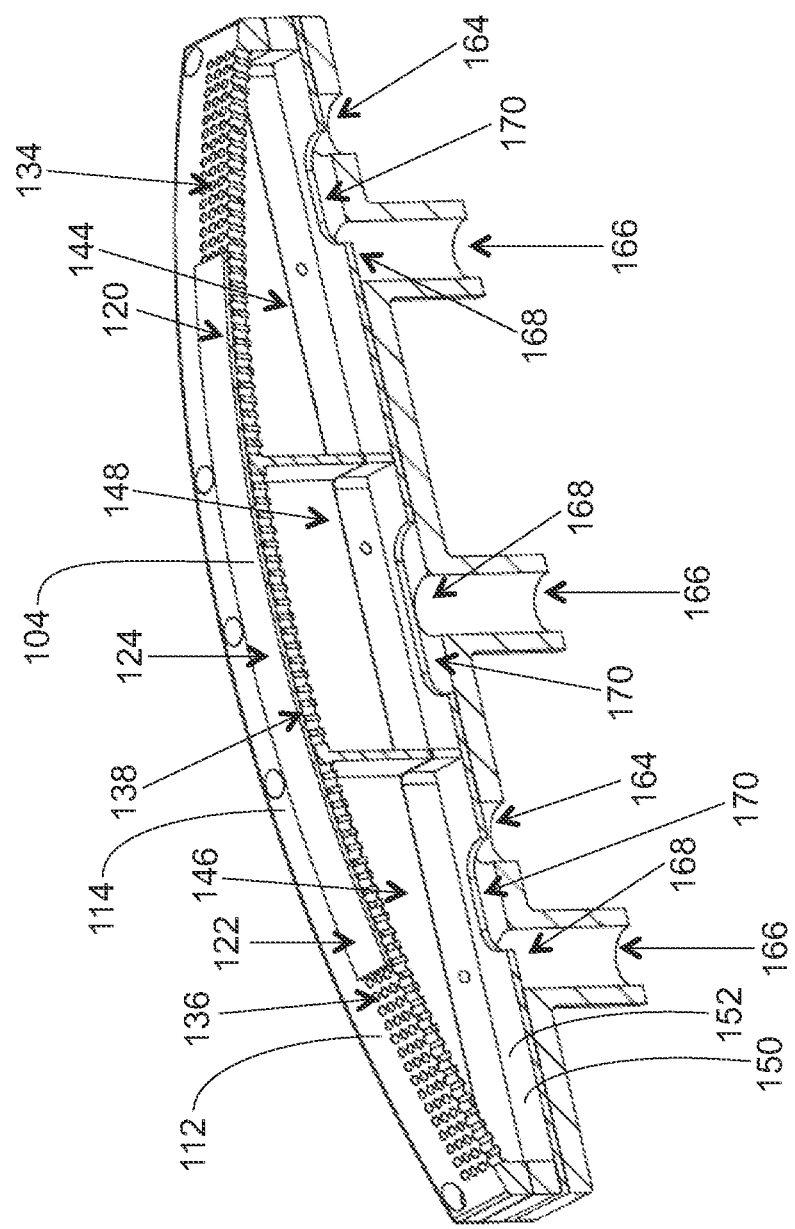
FIG. 4B is a partial, cross-sectional view of a drum having slide bar vacuum control member.

The drum 112 may also include a vacuum control member 150, shown in FIG. 4A as a slide bar 152 for exemplary purposes. The slide bar 152 may extend through one or more vacuum compartments and may be disposed along the bottom surface 156 of the vacuum compartments as shown in FIG. 4A. One slide bar 152 may extend along the bottom surface 156 of the first, second, and central vacuum compartments 144, 146, and 148 such that one slide bar 152 adjusts the vacuum pressure applied to one discrete length of elastic substrate 104. The slide bar 152 may comprise a vacuum control aperture 170 located relatively near each vacuum channel opening 168 and vacuum release aperture 164. The slide bar 152 may move back and forth and may be positioned to cover or expose the first, second, and/or central vacuum compartments 144, 146, 148 to the vacuum release aperture 164 and/or the vacuum channel opening 168 with the vacuum control aperture 170. It is to be appreciated that various devices may be operatively connected with the slide bar 152 to move the slide bar 152 back and forth. For example, an electrical or mechanical cam follower, or a solenoid may be used to move the slide bar 152. With reference to FIGS. 4A and 4B, in operation, the slide bar 152 slides back and forth in the direction parallel to the bottom surface 156 of the first, second, and central vacuum compartments 144, 146, and 148. As the slide bar 152 slides, the vacuum control apertures 170 in the slide bar 152 change position relative to the vacuum channel opening 168 and the vacuum release aperture 164 to adjust the vacuum pressure in the first, second, and central vacuum regions 134, 136, and 138.

While it is shown in FIG. 4A that one vacuum control member 150 controls the vacuum pressure of the first, second, and central vacuum compartments 144, 146, and 148, it is to be appreciated that a vacuum control member may control an individual vacuum compartment, or may control two, three, four, or more than four vacuum compartments. The vacuum control member 150 may be configured in various ways. In some exemplary configurations, the vacuum control member may be in the form of a valve that can adjust the vacuum and atmospheric air pressure applied to the vacuum compartment. In some exemplary configurations, more than one vacuum control member 150 may be used.

Referring back to FIGS. 1A, 1B, and 4A, the continuous length of elastic substrate 102 may advance onto the outer circumferential surface 114 of the drum 112 in a stretched state. While advancing on the drum 112, the substrate 102 may be cut into discrete lengths of elastic substrate 104 by a cutting member 116 located adjacent to the drum 112. The discrete length of elastic substrate 104 may be defined by a first end region 120 and a second end region 122 separated by a central region 124. The discrete length of elastic substrate 104 may be positioned on the outer circumferential surface 114 of the drum 112 such that the first end region 120 is positioned on the first vacuum region 134, the second end region 122 is positioned on the second vacuum region 136, and the central region 124 is positioned on the central vacuum region 138. While it is shown in FIG. 4A that a discrete length of elastic substrate 104 covers all of the vacuum apertures 130 in the first, second, and central vacuum regions 134, 136, and 138, it is to be appreciated that a discrete length of elastic substrate 104 may cover only a portion of the vacuum apertures 130 in the first, second, and central vacuum regions 134, 136, and 138.

As shown in FIG. 4A, the slide bar 152 may be positioned such that the vacuum control apertures 170 expose the vacuum channel openings 168 to the first, second, and central vacuum compartments 144, 146, and 148. The drum 112 may be configured to apply vacuum to the first, second, and central vacuum compartments 144, 146, and 148 through the vacuum channels 166. It is to be appreciated that the vacuum apertures 130 in the outer circumferential surface 114 of the drum 112 allow for gaseous communication between the air inside of the first, second, and central vacuum compartments 144, 146, and 148, and the air outside of the outer circumferential surface 114 of the drum 112. As vacuum is pulled in to the first, second, and central vacuum compartments 144, 146, and 148, the vacuum pressure in the first, second, and central vacuum compartments 144, 146, and 148 decreases. In turn, the pressure differential between the first, second, and central vacuum compartments 144, 146, and 148 and the atmospheric air pressure outside of the outer circumferential surface 114 of the drum 112 increases. As a result of the increased pressure differential, the higher atmospheric air pressure forces air toward the lower vacuum pressure in the first, second, and central vacuum compartments 144, 146, and 148, causing the air outside of the outer circumferential surface 114 of the drum 112 to push against the discrete lengths of elastic substrate 104 on the outer circumferential surface 114 of the drum 112. Consequently, the pressure differential holds the discrete lengths of elastic substrate 104 on the outer circumferential surface 114 of the drum 112 in a stretched state. It is to be appreciated that vacuum pressure may not be applied to the first and second end regions 120 and 122 of the discrete length of elastic substrate 104 from the anvil 140 where the continuous length of elastic substrate is cut to the location of the vacuum apertures 130 in the first and second vacuum regions 134 and 136 in closest proximity to the anvils 140. Consequently, portions of the first and second end regions 120 and 122 may consolidate after being cut.

In order to consolidate the discrete length of elastic substrate 104, the slide bar 152 may be positioned such that the vacuum control aperture 170 exposes the first and second vacuum compartments 144 and 146 to the vacuum release aperture 164 as shown in FIG. 4B. In this configuration, the first and second vacuum pressures in the first and second vacuum compartments 144 and 146 increases because the higher, atmospheric air pressure forces air through the vacuum release apertures 164 and into the first and second vacuum compartments 144 and 146. As a result of the increased vacuum pressure in the first and second vacuum compartments 144 and 146, the pressure differential decreases between the first and second vacuum compartments 144 and 146, and the atmospheric air pressure outside of the outer circumferential surface 114 of the drum 112. The pressure differential may be reduced until the force of the air pushing against the discrete length of elastic substrate is insufficient to hold the stretch in the discrete length of elastic substrate 104 at the first length L1 as shown in FIG. 2B. As shown in FIG. 4B, the increased vacuum pressure in the first and second vacuum compartments 144 and 146 causes the first and second end regions 120 and 122 to consolidate or relax while the central region 124 remains at the same elongation, which in turn causes the overall discrete length of elastic substrate 104 to consolidate. Accordingly, and the overall length of the discrete length of elastic substrate 104 reduces from a first length, L1, such as shown in FIG. 2B, to a second length, L2, such as shown in FIG. 2C. In some exemplary configurations, after the discrete length of elastic substrate 104 consolidates, vacuum pressure may be decreased in the first and second vacuum regions 134 and 136 to hold the discrete length of elastic substrate 104 on the outer circumferential surface 114 of the drum 112 at the second length L2.

The vacuum control member may be configured to adjust the first, second, and central vacuum compartments to have different vacuum pressures. As shown in FIGS. 4A and 4B, the slide bar 152 may be configured such that the vacuum control aperture 170 exposes the central vacuum compartment 148 to the vacuum channel opening while the slide bar 152 exposes the first and second vacuum compartments 144 and 146 to the vacuum channel openings 168 and the vacuum release apertures 164. As shown in FIGS. 4A and 4B, in some exemplary configurations the central vacuum compartment 148 may not be configured with a vacuum release aperture 164 in order to maintain a relatively low vacuum pressure in the central vacuum compartment 148. Therefore, the central vacuum compartment 148 may be maintained at a vacuum pressure low enough to hold the central region 124 of the discrete length of elastic substrate 104 in a stretched state while the discrete length of elastic substrate advances on the outer circumferential surface 114 of the drum 112.

While it is shown in FIGS. 4A and 4B that the central vacuum compartment 148 may not include a vacuum release aperture 164, it is to be appreciated that the first, second, and central vacuum compartments 144, 146, and 148 may be configured in various ways. For example, each vacuum compartment may include both a vacuum channel opening 168 and a vacuum release aperture 164, or some vacuum compartments may only include a vacuum channel opening 168 or a vacuum release aperture 164. In addition, as shown in FIG. 4B, the vacuum control member 150 may be configured such that the vacuum control aperture 170 may expose the first and second vacuum compartments 144 and 146 to both the vacuum channel opening and the vacuum release opening. It is to be appreciated that the vacuum pressure may increase relatively faster if a vacuum compartment is exposed to vacuum through the vacuum channel opening 168 and atmospheric air pressure through the vacuum release opening 164 than if the vacuum compartment was exposed only to the atmospheric air pressure through the vacuum release opening 164.

With reference back to FIGS. 1A and 1B, once the discrete length of elastic substrate is consolidated, the drum 112 may continue rotating and the discrete length of elastic substrate 104 having a length L2 may be released from the outer circumferential surface 114 of the drum 112 to another operation and/or to be joined with another substrate. The vacuum pressure may be increased in the first, second, and central vacuum compartments 144, 146, and 148 in order for the discrete length of elastic substrate 104 to be removed from the outer circumferential surface 114 of the drum 112. In some exemplary configurations, the discrete length of elastic substrate 104 may be joined to a substrate advancing in a cross direction relative to the direction of the advancing discrete length of elastic substrate 104.

While FIGS. 4A and 4B show one first vacuum compartment 144, one second vacuum compartment 146, and one central vacuum compartment 148, it is to be appreciated that the drum 112 may include more than one first, second, and central vacuum compartment for consolidating subsequent discrete lengths of elastic substrate that may advance on the outer circumferential surface 114 of the drum 112. In addition, each first, second, and central vacuum compartment may be in gaseous communication with a first, second, and central region of vacuum apertures, respectively. As such, the continuous length of elastic substrate may be positioned on the drum such that one discrete length of elastic substrate may be positioned on a first, second, and central vacuum region, and a subsequent discrete length of elastic substrate may be positioned on a subsequent first, second, and central vacuum region. Exemplary rotary drums are described in U.S. Provisional Patent Application No. 61/665,938.

Figure 5A:
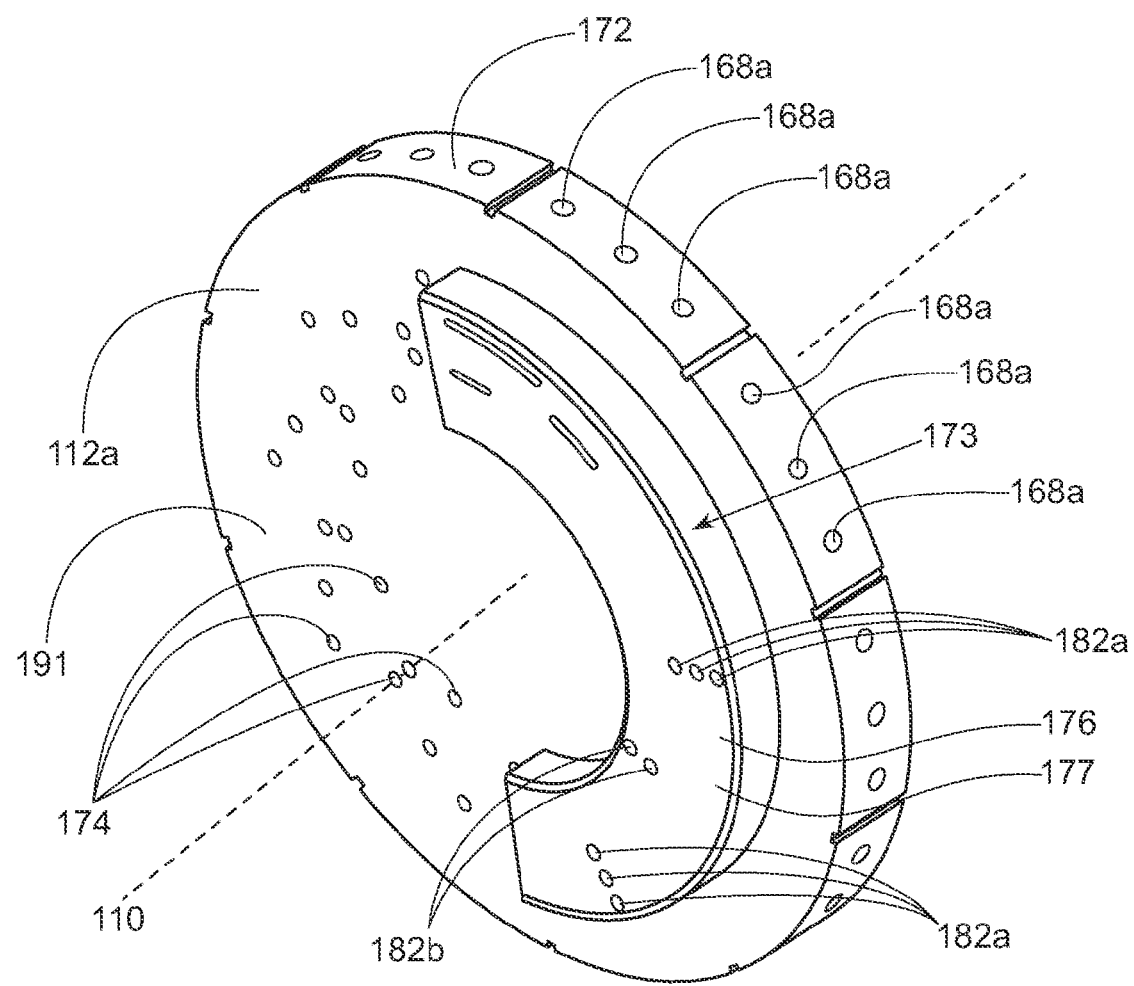
FIG. 5A is a perspective, side view of a first member of a rotary vacuum control member connected with a drum.
Figure 5B:
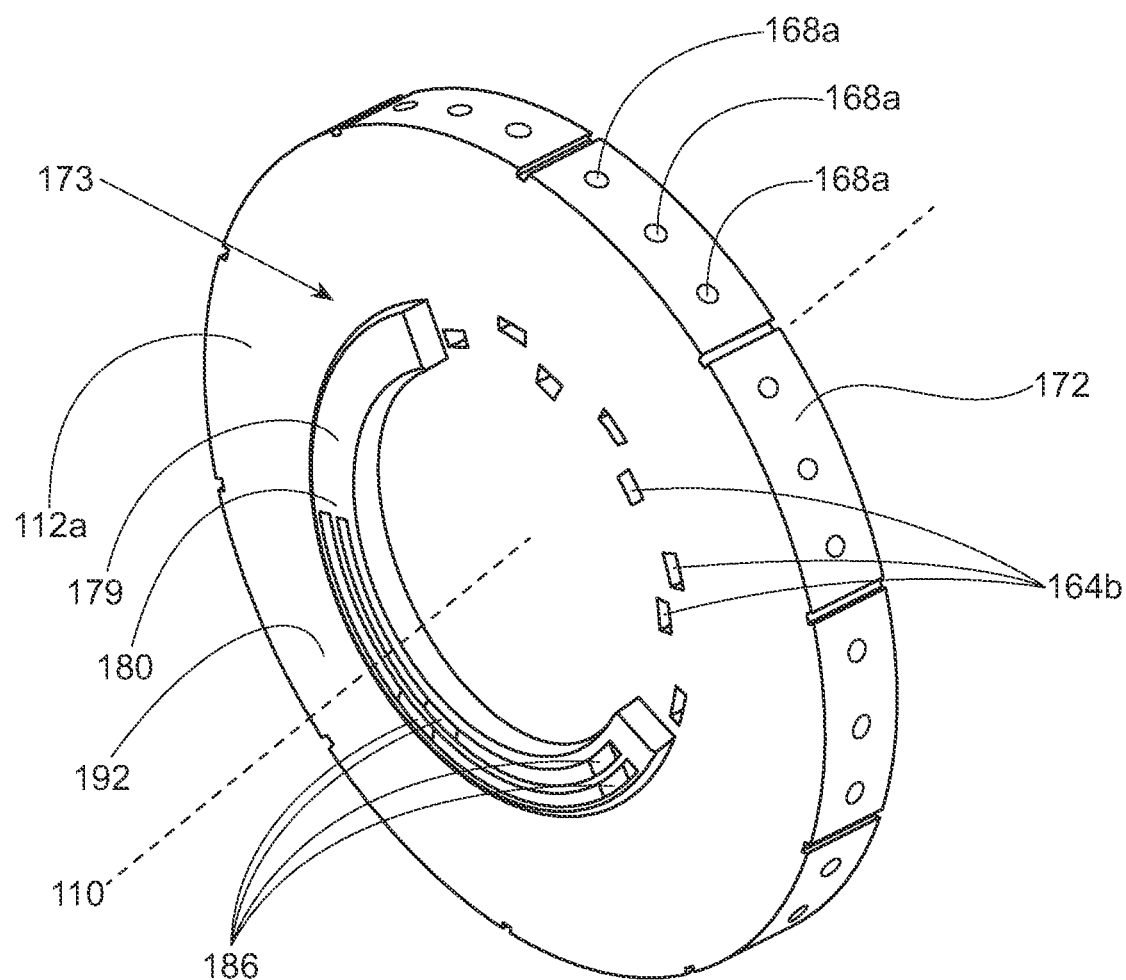
FIG. 5B is a perspective, side view of a second member of a rotary vacuum control member connected with a drum.

In some exemplary configurations, the vacuum control member may be in the form of a rotary vacuum control member such as shown in FIGS. 5A and 5B. With reference to FIGS. 5A and 5B, a drum 112a may define a first side 191, a second side 192, and an inner circumferential surface 172. A rotary vacuum control member 173 may be located adjacent the drum 112a and may include a first member 176 located adjacent the first side 191 of the drum 112a and a second member 179 located adjacent the second side 192 of the drum 112a. The drum 112a may include a plurality of vacuum inlet apertures 174 located on the first side 191 of the drum 112a and a plurality of vacuum release apertures 164b located on the second side 192 of the drum 112a. The vacuum inlet apertures 174 and vacuum release apertures 164b may be in gaseous communication with a vacuum channel 166a located inside of the drum 112 that opens to the inner circumferential surface 172 of the drum 112a at the vacuum channel openings 168a as shown in FIG. 5D. The first member 176 of the rotary vacuum control member 173 may include a plurality of vacuum inlets 182a and 182b. The second member 179 of the rotary vacuum control member 173 may include a plurality of air inlets 186.

Figure 5C:
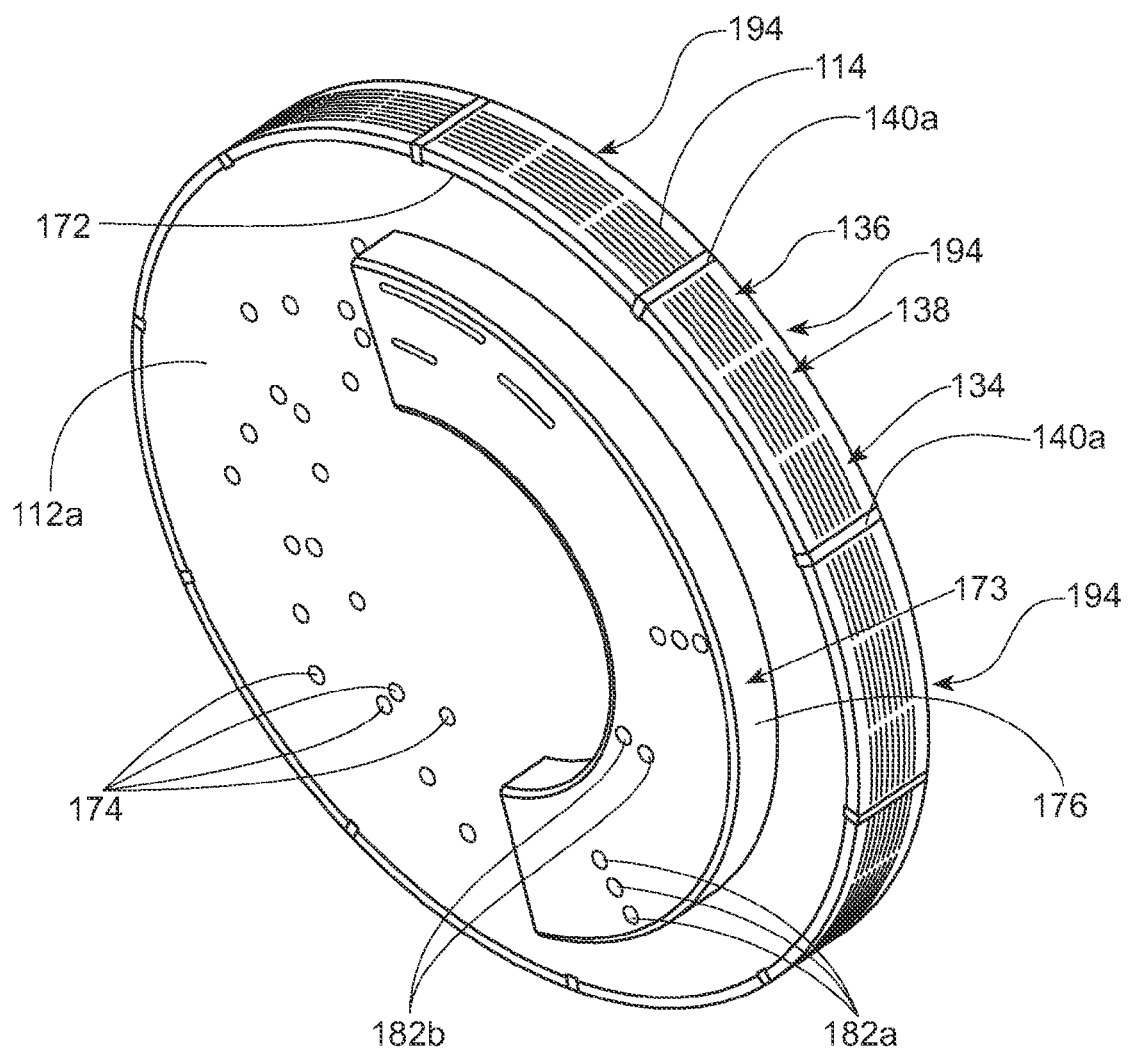
FIG. 5C is a perspective, side view of a drum having a rotary vacuum control member.
Figure 5D:
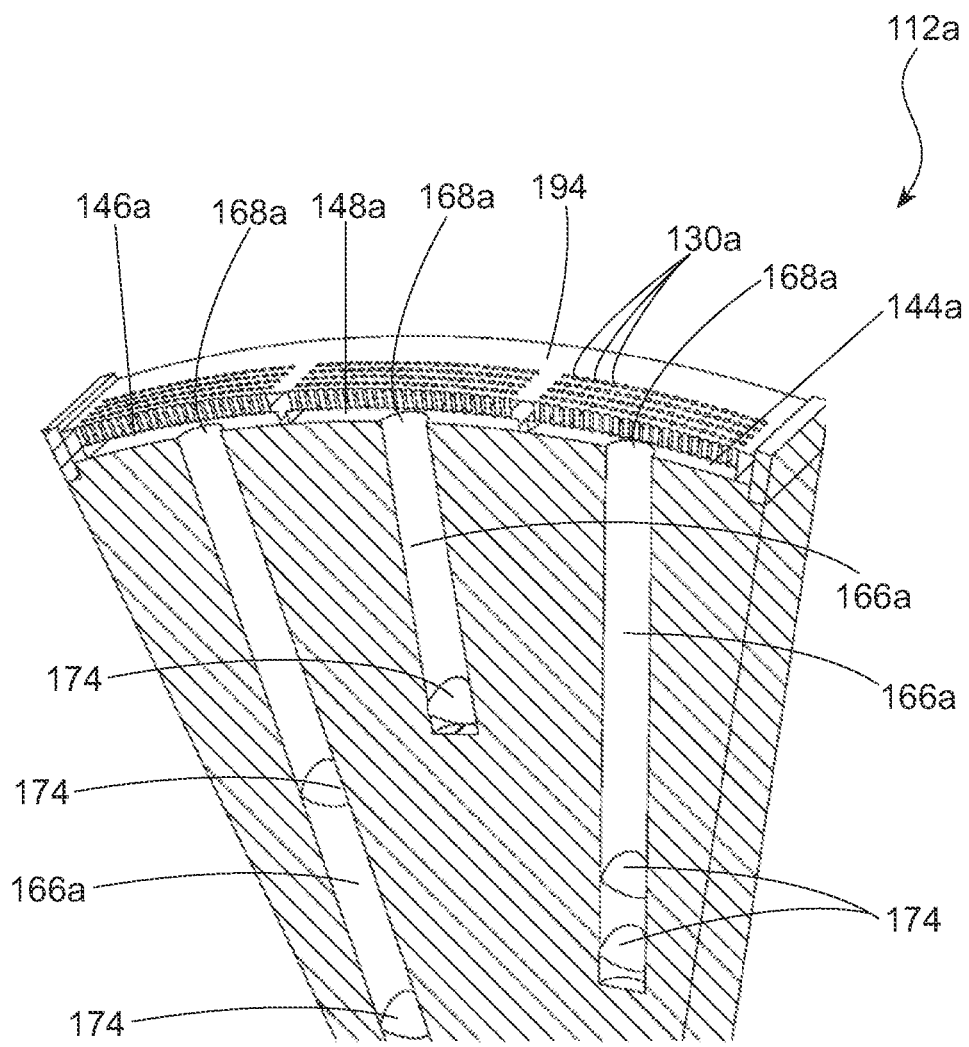
FIG. 5D is a partial, cross-sectional view of a drum having a rotary vacuum control member.
Figure 5E:
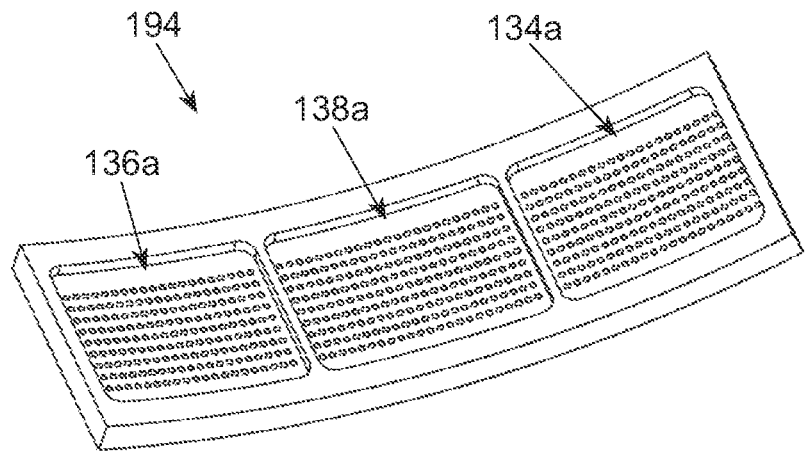
FIG. 5E is a perspective, bottom view of a vacuum segment.
Figure 5F:
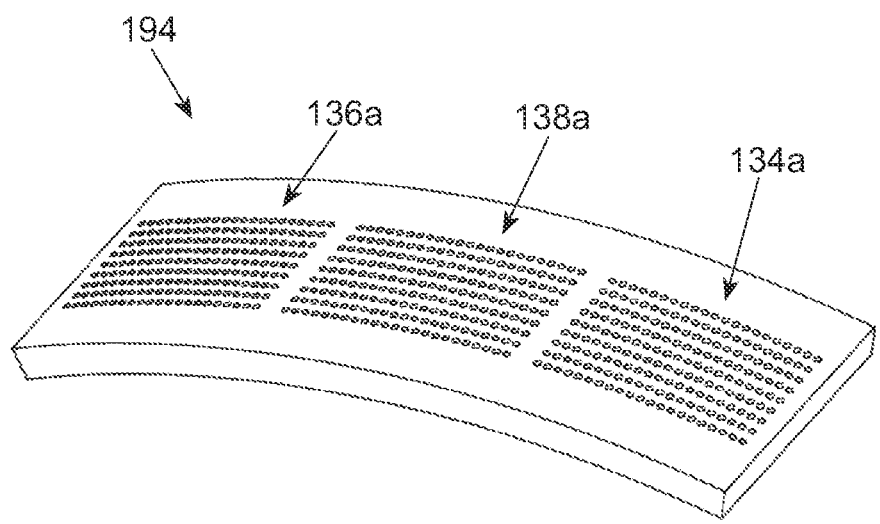
FIG. 5F is a perspective, top view of a vacuum segment.

As shown in FIG. 5C, the drum 112a includes vacuum segments 194 and anvils 140a that form the outer circumferential surface 114 of the drum 112a. Each vacuum segment 194, such as the vacuum segment 194 shown in FIGS. 5E and 5F, connects with the inner circumferential surface 172 of the drum 112a to form a first vacuum compartment 144a, a second vacuum compartment 146a, and a central vacuum compartment 148a as shown in FIG. 5D. With reference to FIGS. 5A, 5C, and 5D, the vacuum inlet apertures 174 are in gaseous communication with vacuum channels 166a. The vacuum channels 166a have vacuum channel openings 168a that open into the first, second, and central vacuum compartments 144a, 146a, and 148a at the inner circumferential surface 172 of the drum 112a. The first, second, and central vacuum compartments 144a, 146a, and 148a may be in gaseous communication with a first, second, and central vacuum regions 134a, 136a, and 138a of vacuum apertures 130a, respectively. The vacuum release apertures 164b are also in gaseous communication with the vacuum channels 166a that are in gaseous communication with the first and second vacuum compartments 144a and 146a.

Figure 5G:
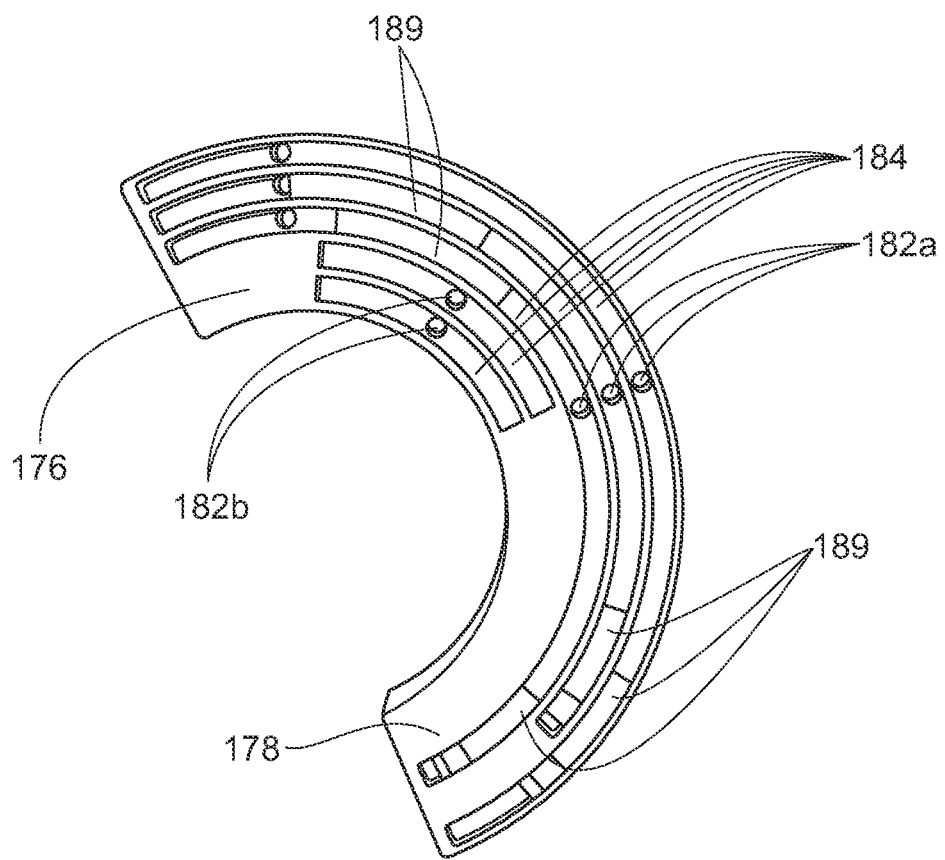
FIG. 5G is a side, elevation view of a first member of a rotary vacuum control member.
Figure 5H:
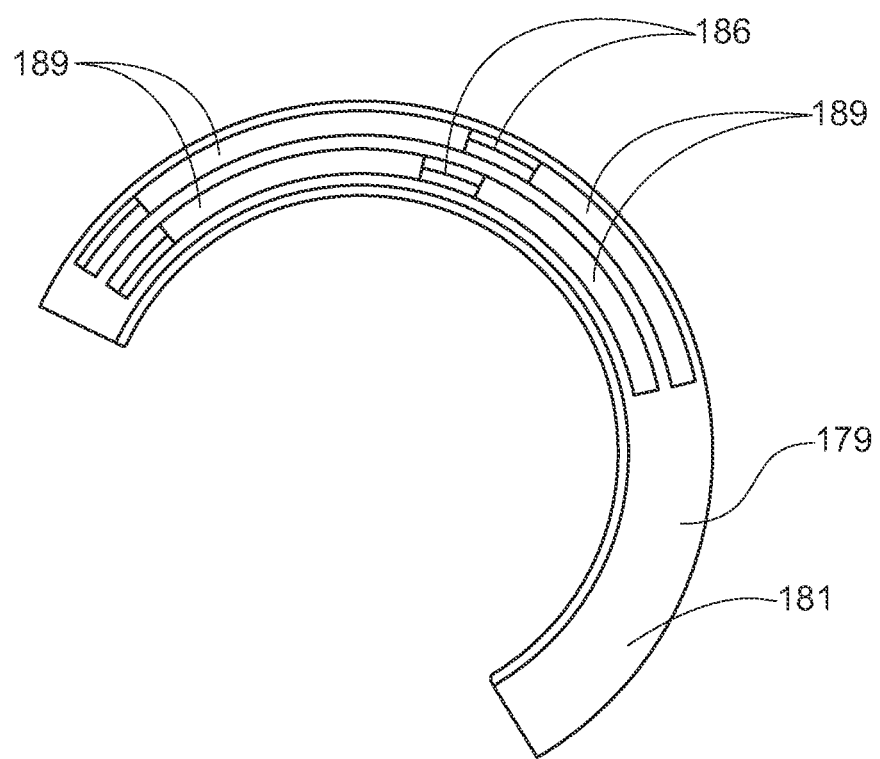
FIG. 5H is a side, elevation view of a second member of a rotary vacuum control member.

As shown in FIG. 5G, the first member 176 may include vacuum inlets 182a and 182b that connect with first member vacuum channels 184 as can be seen from outer and inner sides 177, 178 of the first member 176 as shown in FIGS. 5A and 5G. The second member 179 may include air inlets 186 as can be seen from outer and inner sides 180, 181 of the second member 179 as shown in FIGS. 5B and 5H. The first and second members 176, 179 may include channel blocks 189 that block the flow of air in certain regions of the first and second member 176, 179 as shown in FIGS. 5G and 5H.

In operation, with continuing reference to FIGS. 5A, 5B, 5D, the drum 112a rotates about the axis of rotation 110 while the first and second members 176, 179 of the rotary vacuum control member 173 remain stationary. To decrease the vacuum pressure in the vacuum compartments, vacuum is applied through the vacuum inlets 182a. Vacuum inlets 182a apply vacuum to the first, second, and central vacuum compartments 144a, 146a, and 148a for reducing the vacuum pressure in the vacuum compartments while vacuum inlets 182b apply vacuum to the first and second vacuum compartments when the air inlets 186 are exposed to atmospheric air pressure in order to increase vacuum pressure in the vacuum compartments. Vacuum is applied through the vacuum inlets 182a, then through first member vacuum channels 184, through vacuum inlet apertures 174 in the drum 112a, through vacuum channels 166a in the drum 112a, through the vacuum channel openings 168a, and to the first, second, and central vacuum compartments 144a, 146a, 148a. In order to increase the vacuum pressure in the vacuum compartments, air outside of the drum 112a may be forced by atmospheric air pressure into the air inlets 186, through the vacuum release apertures 164b of the drum 112a, through vacuum channels 166a to the vacuum channel openings 168a, and into the first and second vacuum compartments 144a and 146a. At the same time that air enters the first and second vacuum compartments 144a and 146a to increase the vacuum pressure, vacuum may be applied through the vacuum inlets 182b, through the first member vacuum channels 184, through vacuum inlet apertures 174 in the drum 112a, through vacuum channels 166a, through the vacuum channel openings 168a to the first and second vacuum compartments 144a and 146a. It is to be appreciated that the position of the drum 112a with respect to the first and second members 176 and 179 of the rotary vacuum control member 173, respectively, determines when vacuum is applied to the first, second, and third vacuum compartments 144a, 146a, and 148a and when the first and second vacuum compartments 144a and 146a are exposed to atmospheric air pressure.

It is to be appreciated that the elastic substrate may include various materials. For example, the elastic substrate may include a first substrate layer and a second substrate layer separated by an elastic material. The elastic material may be in the form of elastic strands, ribbons, films, or combinations thereof. The elastic material may include one or a plurality of elastic strands, ribbons, and/or films. In some exemplary configurations, the elastic strands and/or ribbons may be longitudinally spaced at constant intervals. Or, in some exemplary configurations, the elastic strands and/or ribbons may be longitudinally spaced at different intervals. The elastic material may have a decitex in the range of about 480 to about 1520. In some exemplary configurations, a layered elastic substrate may comprise elastic materials of various decitex values. The elastic strands may have various diameters and cross-sectional geometry.

The first and/or second substrate layers may include woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some exemplary configurations, the first and/ or the second substrate layers may include a polymeric film (e.g., polyethylene or polypropylene). In some exemplary configurations, the first and/or second substrate layers may include a stretchable material. Various methods and apparatuses for forming a layered elastic substrate are described in U.S. Provisional Patent Application No. 61/665,942, and U.S. Provisional Patent Application No. 61/665,945.

It is to be appreciated that the vacuum pressure needed to consolidate regions of a discrete length of elastic substrate may depend upon the percent elongation of the discrete length of elastic substrate and the mechanical properties of the discrete length of elastic substrate. For example, in the case of a discrete length of elastic substrate stretched to a relatively high elongation, a relatively low vacuum pressure is needed to maintain stretch in the discrete length of elastic substrate compared with the vacuum pressure required for a material stretched to a relatively low percent elongation. Similarly, a discrete length of elastic substrate having a stronger, higher decitex elastic material may require a relatively low vacuum pressure in order to maintain stretch in the discrete length of elastic substrate compared with a discrete length of elastic substrate having a weaker, lower decitex elastic material.

It is to be appreciated that the distance of the vacuum release aperture from the vacuum compartment may affect the amount of time it takes for the vacuum pressure in the vacuum compartment to increase. For example, when the vacuum release aperture is located within a vacuum compartment such as shown in FIGS. 4A and 4B, and thus relatively close to the vacuum compartment, opening or closing the vacuum release aperture has a relatively fast effect on the vacuum pressure in the vacuum compartment. On the other hand, when the vacuum release aperture is located away from the vacuum compartment, such as shown in FIGS. 5A-5H, and thus further away from the vacuum compartment, opening or closing the vacuum release aperture has a relatively slow effect on the vacuum pressure in the vacuum compartment.

It is to be appreciated that the vacuum pressure in the vacuum compartment may increase relatively faster if the vacuum channel opening and the vacuum release aperture are both at least partially exposed to the vacuum compartment than if the vacuum channel opening is covered when vacuum release aperture is open. In the case of an air permeable elastic substrate advancing on the drum, vacuum pressure in the vacuum compartment may be increased by covering the vacuum channel opening to the vacuum compartment, and without opening the vacuum release aperture. It is to be appreciated that in the case of an air permeable elastic substrate, atmospheric air pressure may force air onto the vacuum compartment through the air permeable elastic substrate on the outer circumferential surface of the drum, thereby increasing the vacuum pressure in the vacuum compartment while the vacuum channel opening and vacuum release opening are covered to the vacuum compartment.

In some exemplary configurations, in the case of an air impermeable elastic substrate, the vacuum regions may be configured such that the discrete length of elastic substrate only covers a portion of the vacuum apertures in the first, second, and central vacuum regions in order to assist the discrete length of elastic substrate in releasing from the drum.

As previously mentioned, each vacuum region of vacuum apertures may be in gaseous communication with a separate vacuum compartment to apply different vacuum pressure to different regions of the discrete length of elastic substrate. However, in some exemplary configurations, a single discrete length of elastic substrate may be in contact with more or less than three vacuum regions and/or vacuum compartments.

In some exemplary configurations, the apparatus may be configured so that vacuum pressure applied to the first, second, and central regions is relatively low when the stretched elastic substrate is cut into discrete lengths of elastic substrate. In this exemplary configuration, as the elastic substrate is advanced onto the drum, the first, second, and central vacuum regions are configured to apply low vacuum pressure to hold the discrete lengths of elastic substrate in a stretched state once the discrete lengths of elastic substrate are cut. Once the discrete length of elastic substrate is cut, vacuum pressure in the first and second vacuum compartments may be increased in the first and second vacuum regions. As a result, the discrete length of elastic substrate may consolidate in the first and second end regions and the discrete length of elastic substrate may be reduced in length from a first length to a second length. In some exemplary configurations, after the discrete length of elastic substrate relaxes to a second length, vacuum pressure is decreased in the first and second vacuum regions in order to hold the discrete length of elastic substrate stretched at the second length.

In another exemplary configuration, the apparatus may be configured to increase the vacuum pressure in the first and second vacuum compartments and decrease the vacuum pressure in the central vacuum compartment before the stretched elastic substrate is cut into discrete lengths of elastic substrate. As a result of the increased vacuum pressure in the first and second vacuum regions, once the elastic substrate is cut, the first and second end regions of the discrete length of elastic substrate consolidate while the central region maintains stretched. Thus, the discrete length of elastic substrate may consolidate from a first length to a second length. In some exemplary configurations, after the discrete length of elastic substrate may consolidate to a second length vacuum pressure may be decreased in the first and second vacuum regions in order to maintain the discrete length of elastic substrate at the second length.

In some exemplary configurations, the vacuum pressure applied in the first, second, and central vacuum compartments may be greater than 10,000 Pascals (Pa), or may be greater than 15,000 Pa, or may be greater than 20,000 Pa. In other exemplary configurations, in order to consolidate the discrete length of elastic substrate in the first and second end regions, the vacuum pressure in the first and second vacuum compartments may be less than about 7,500 Pa, or may be less than about 5,000 Pa, or may be less than about 2,500 Pa and the vacuum pressure in the central vacuum compartment may be greater than 10,000 Pa, or may be greater than 15,000 Pa, or may be greater than 20,000 Pa, for example. Before consolidating regions of the discrete length of elastic substrate, the discrete length of elastic substrate may have an elongation of 150% at the first length. In some exemplary configurations, after the discrete length of elastic substrate consolidates, the discrete length of elastic substrate may have an elongation of 80% at the second length. It is to be appreciated that the discrete length of elastic substrate may have an elongation of about 200%, 190%, 180%, 170%, 160%, 150%, 140%, 130%, 120%, 110%, or 100% at the first length and may have an elongation of about 10%, 20%, 30%, 40%, 50%, 60%, 70%, 80%, 90%, 100% at the second length.

The processes and apparatuses discussed herein may be used to assemble discrete lengths of elastic substrate with various configurations, some of which may be used in the manufacture of different types of absorbent articles. To help provide additional context to the subsequent discussion of the process embodiments, the following provides a general description of absorbent articles in the form of diapers that include discrete lengths of elastic substrate in the form of elastic waistbands that may be assembled in accordance with the methods and apparatuses disclosed herein.

Figure 6:
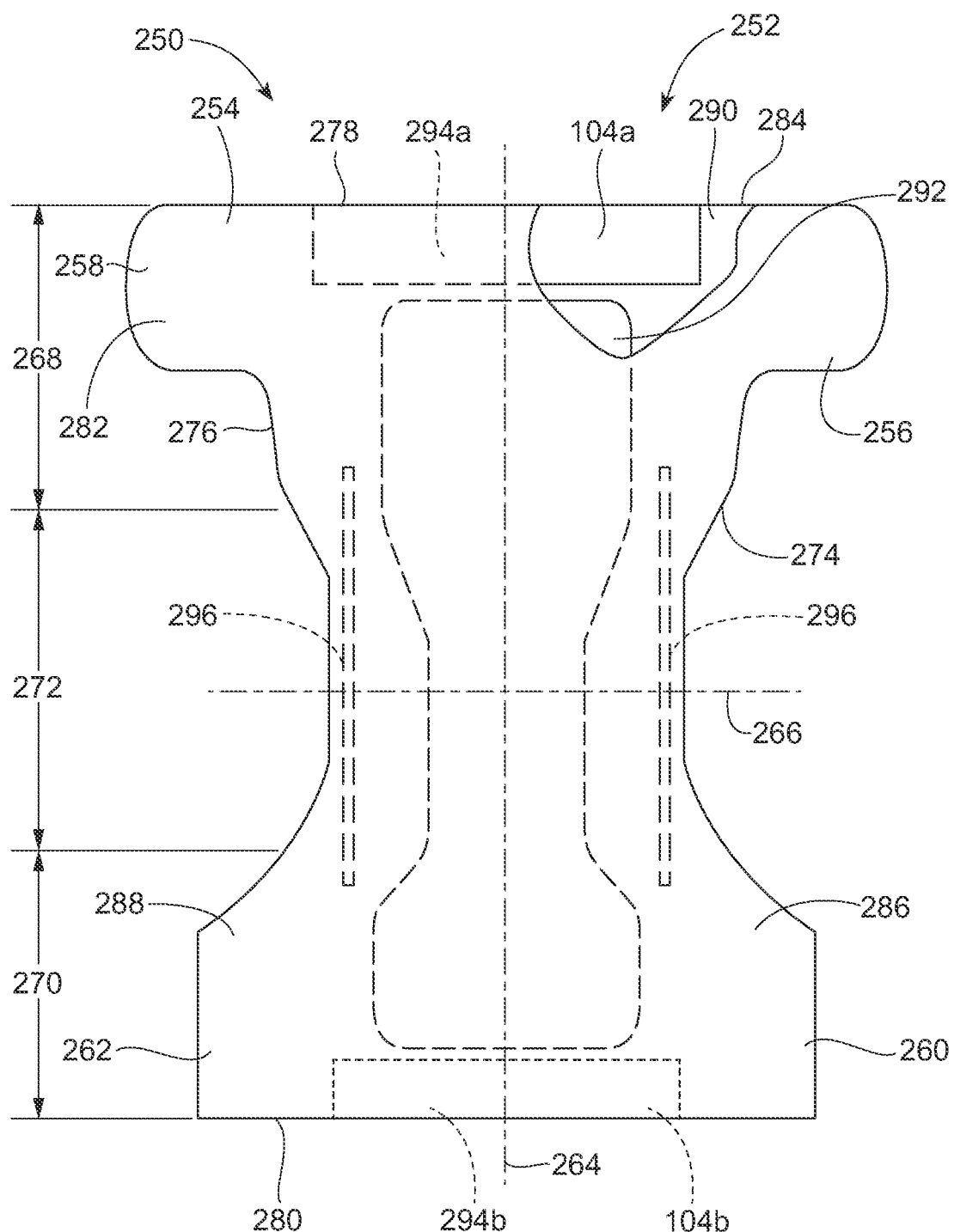
FIG. 6 is a partially cut-away, plan view of a disposable absorbent article having discrete waistbands.

For the purposes of a specific illustration, FIG. 6 shows one example of a disposable absorbent article 250 in the form of a diaper 252 that may include discrete lengths of elastic substrate 104a and 104b formed in accordance with methods and apparatuses of the present disclosure. In particular, FIG. 6 is a plan view of one embodiment of a diaper 252 including a chassis 254 shown in a flat, unfolded condition, with the portion of the diaper 252 that faces a wearer oriented towards the viewer. A portion of the chassis structure is cut-away in FIG. 6 to more clearly show the construction of and various features that may be included in exemplary configurations of the diaper.

As shown in FIG. 6, the diaper 252 includes a chassis 254 having a first ear 256, a second ear 258, a third ear 260, and a fourth ear 262. To provide a frame of reference for the present discussion, the chassis is shown with a longitudinal axis 264 and a lateral axis 266. The chassis 254 is shown as having a first waist region 268, a second waist region 270, and a crotch region 272 disposed intermediate the first and second waist regions. The periphery of the diaper is defined by a pair of longitudinally extending side edges 274, 276; a first outer edge 278 extending laterally adjacent the first waist region 268; and a second outer edge 280 extending laterally adjacent the second waist region 270. As shown in FIG. 6, the chassis 254 includes an inner, body-facing surface 282, and an outer, garment-facing surface 284. A portion of the chassis structure is cut-away in FIG. 6 to more clearly show the construction of and various features that may be included in the diaper. As shown in FIG. 6, the chassis 254 of the diaper 252 may include an outer covering layer 286 including a topsheet 288 and a backsheet 290. An absorbent core 292 may be disposed between a portion of the topsheet 288 and the backsheet 290. One or more of the regions may be stretchable and may include an elastomeric material or discrete length of elastic substrate as described herein. As such, the diaper 252 may be configured to adapt to a specific wearer's anatomy upon application and to maintain coordination with the wearer's anatomy during wear.

Although the first and second ears 256, 258 as well as the third and fourth ears 260, 262 shown in FIG. 6 are illustrated as being integrally formed with the chassis 254, it is to be appreciated that other embodiments may include ears that are discrete elements connected with the chassis. In some embodiments, the ears are configured to be stretchable. The ears may also include one or more fastener elements adapted to releasably connect with each other and/or other fastener elements on the chassis. A more detailed discussion of stretchable ears can be found in U.S. Pat. Nos. 4,857,067; 5,151,092; 5,674,216; 6,677,258; 4,381,781; 5,580,411; and 6,004,306. The ears may also include various geometries and arrangements of stretch zones or elements, such as discussed in U.S. Pat. Publication Nos. US2005/0215972A1 and US2005/0215973A1.

As shown in FIG. 6, the diaper 252 may include leg cuffs 296 that may provide improved containment of liquids and other body exudates. The leg cuffs 296 may be disposed in various ways on the diaper 252. For example, the leg cuffs 296 may be disposed on the outer, garment-facing surface 284 of the chassis 254; the inner, body-facing surface 282; or between the inner and outer facing surfaces 282 or 284. Leg cuffs 296 may also be referred to as leg bands, side flaps, barrier cuffs, or elastic cuffs. U.S. Pat. No. 3,860,003 describes a disposable diaper that provides a contractible leg opening having a side flap and one or more elastic members to provide an elasticized leg cuff (a gasketing cuff). U.S. Pat. Nos. 4,808,178 and 4,909,803 describe disposable diapers having "stand-up" elasticized flaps (barrier cuffs). U.S. Pat. Nos. 4,695,278 and 4,795,454 describe disposable diapers having dual cuffs, including gasketing cuffs and barrier cuffs.

The diaper may be provided in the form of a pant-type diaper or may alternatively be provided with a re-closable fastening system, which may include fastener elements in various locations to help secure the diaper in position on the wearer. For example, fastener elements may be located on the first and second ears and may be adapted to releasably connect with one or more corresponding fastening elements located in the second waist region. It is to be appreciated that various types of fastening elements may be used with the diaper. In one example, the fastening elements include hook & loop fasteners, such as those available from 3M or Velcro Industries. In other examples, the fastening elements include adhesives and/or tap tabs, while others are configured as a macrofastener or hook (e.g., a MACRO or "button-like" fastener). Some exemplary fastening elements and systems are disclosed in U.S. Pat. Nos. 3,848,594; 4,662,875; 4,846,815; 4,894,060; 4,946,527; 5,151,092; and 5,221,274. Additional examples of fasteners and/or fastening elements are discussed in U.S. Pat. Nos. 6,251,097 and 6,432,098; and U.S. Patent Publication Nos. 2007/0078427 and 2007/0093769. Other fastening systems are described in more detail in U.S. Pat. Nos. 5,595,567; 5,624,427; 5,735,840; and 5,928,212. The fastening system may also provide a means for holding the article in a disposal configuration as disclosed in U.S. Pat. No. 4,963,140.

Components of the disposable absorbent article (i.e., diaper, disposable pant, adult incontinence article, sanitary napkin, pantiliner, etc.) described in this specification can at least partially be comprised of bio-sourced content as described in US 2007/0219521A1 Hird et al published on Sep. 20, 2007, US 2011/0139658A1 Hird et al published on Jun. 16, 2011, US 2011/0139657A1 Hird et al published on Jun. 16, 2011, US 2011/0152812A1 Hird et al published on Jun. 23, 2011, US 2011/0139662A1 Hird et al published on Jun. 16, 2011, and US 2011/0139659A1 Hird et al published on Jun. 16, 2011. These components include, but are not limited to, topsheet nonwovens, backsheet films, backsheet nonwovens, side panel nonwovens, barrier leg cuff nonwovens, super absorbent, nonwoven acquisition layers, core wrap nonwovens, adhesives, fastener hooks, and fastener landing zone nonwovens and film bases.

In at least one exemplary configuration, a disposable absorbent article component comprises a bio-based content value from about 10% to about 100% using ASTM D6866-10, method B, in another embodiment, from about 25% to about 75%, and in yet another embodiment, from about 50% to about 60% using ASTM D6866-10, method B.

In order to apply the methodology of ASTM D6866-10 to determine the bio-based content of any disposable absorbent article component, a representative sample of the disposable absorbent article component must be obtained for testing. In at least one embodiment, the disposable absorbent article component can be ground into particulates less than about 20 mesh using known grinding methods (e.g., Wiley® mill), and a representative sample of suitable mass taken from the randomly mixed particles.

The absorbent article may also include discrete lengths of elastic substrate 104a and 104b such as shown in FIG. 6 in the form of first and second waistbands 294a and 294b. The first and second waistbands 294a and 294b may provide improved fit and waste containment. The first and second waistbands 294a and 294b may be located in the first waist region 268 and/or the second waist region 270. The first and second waistbands 294a and 294b may be configured to elastically expand and contract to dynamically fit the wearer's waist.

The first and second waistbands 294a and 294b can be incorporated into the diaper in accordance with the methods discussed herein and may extend at least longitudinally outwardly from the absorbent core 292 and generally form at least a portion of the first and/or second outer edges 278, 280 of the diaper 252. In addition, the first and second waistbands 294a and 294b may extend laterally to include the ears. While the first and second waistbands 294a and 294b or any constituent elements thereof may comprise one or more separate elements affixed to the diaper, the first and second waistbands 294a and 294b may be constructed as an extension of other elements of the diaper, such as the backsheet 290, the topsheet 288, or both the backsheet 290 and the topsheet 288. In addition, the first and second waistbands 294a and 294b may be disposed on the outer, garment-facing surface 284 of the chassis 254; the inner, body-facing surface 282; or between the inner and outer facing surfaces. It is to be appreciated that the first waistband 294a and the second waistband 294b shown in FIG. 6 may comprise the same materials and/or may have the same structure. While in other exemplary configurations, the first waistband 294a and the second waistband 294b may comprise different materials and/or may have different structures. The first and second waistbands 294a and 294b may be constructed in a number of different configurations including those described in U.S. Patent Application No. 61/499,294; and U.S. Patent Publication Nos. 2007/0142806; 2007/0142798; and 2007/0287983.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for consolidating a discrete length of elastic substrate, the method comprising the steps of:
    rotating a drum about a rotation axis, the drum having an outer circumferential surface;
    positioning a discrete length of elastic substrate on the outer circumferential surface of the rotating drum, wherein the discrete length of elastic substrate is in a stretched state and defines a first length, the discrete length of elastic substrate having a first end region, a second end region, and a central region separating the first and second end regions;
    applying vacuum pressure to the first end region, second end region, and central region of the discrete length of elastic substrate, wherein the vacuum pressures on the first end region, second end region, and central region of the discrete length of elastic substrate are less than atmospheric air pressure; and changing the vacuum pressure on the first and second end regions such that the discrete length of elastic substrate consolidates to a second length that is less than the first length.

2. The method of claim 1, further comprising the step of: applying a first vacuum pressure to the first end region; applying a second vacuum pressure to the second end region; and applying a third vacuum pressure to the central region.

3. The method of claim 2, further comprising the step of: increasing the first and second vacuum pressures above the third vacuum pressure.

4. The method of claim 1, further comprising the steps of advancing a continuous length of elastic substrate in a machine direction; and cutting the continuous length of elastic substrate into discrete lengths of elastic substrate.

5. The method of claim 4, further comprising the steps of advancing the continuous length of elastic substrate onto the outer circumferential surface of the drum; and cutting the continuous length of elastic substrate while positioned on the outer circumferential surface of the drum.

6. The method of claim 4, further comprising the step of advancing the discrete length of elastic substrate onto the outer circumferential surface of the drum.

7. The method of claim 1, further comprising the step of decreasing the vacuum pressure on the first and second end regions.

8. The method of claim 2, wherein the first vacuum pressure is greater than about 10,000 Pascals, the second vacuum pressure is greater than about 10,000 Pascals, and the third vacuum pressure is greater than about 10,000 Pascals.

9. The method of claim 2, wherein the first vacuum pressure is less than about 7,500 Pascals, the second vacuum pressure is less than about 7,500 Pascals, and the third vacuum pressure is greater than about 10,000 Pascals.

10. The method of claim 1, wherein the discrete length of elastic substrate has a 150% elongation at the first length, and wherein the discrete length of elastic substrate has an 80% elongation at the second length.

11. The method of claim 1, wherein the drum further comprises:
a plurality of vacuum apertures in the outer circumferential surface of the drum, wherein the vacuum apertures are arranged into a first vacuum region, a second vacuum region, and a central vacuum region
a first vacuum compartment located radially inward from the outer circumferential surface of the drum, wherein the vacuum apertures in the first vacuum region are in gaseous communication with the first vacuum compartment;
a second vacuum compartment located radially inward from the outer circumferential surface of the drum, wherein the vacuum apertures in the second vacuum region are in gaseous communication with the second vacuum compartment, wherein the first and second vacuum compartments each comprise a vacuum release aperture;
a third vacuum compartment located radially inward from the outer circumferential surface of the drum, wherein the vacuum apertures in the central vacuum region are in gaseous communication with the third vacuum compartment, wherein the first, second, and third vacuum compartments each comprise a vacuum channel, each vacuum channel having a vacuum channel opening; and
a vacuum control member located adjacent the vacuum channel openings and the vacuum release apertures, the vacuum control member comprising a plurality of vacuum control apertures.

12. The method of claim 11, wherein the step of positioning the discrete length of elastic substrate on the outer circumferential surface of the drum further comprises:
positioning the first end region of the discrete length of elastic substrate adjacent the first vacuum region in the outer circumferential surface of the drum;
positioning the second end region of the discrete length of elastic substrate adjacent to the second vacuum region in the outer circumferential surface of the drum; and
positioning the central region of the discrete length of elastic substrate adjacent to the central vacuum region in the outer circumferential surface of the drum.

13. The method of claim 12, wherein the step of applying vacuum pressure to the first, second, and central regions of the elastic substrate further comprises changing the vacuum pressure in the first, second, and central vacuum compartments.

14. The method of claim 12, wherein the step of changing the vacuum pressure on the first and second end regions pulls air through the vacuum release apertures into the first and second vacuum compartments.

15. The method of claim 12 further comprising the step of sliding the vacuum control member to cover the vacuum release aperture.

16. The method of claim 12 further comprising the step of sliding the vacuum control member to expose the vacuum release aperture.

* * * * *